United States Patent [19]
Worrel

[11] 3,965,182

[45] June 22, 1976

[54] PREPARATION OF ANILINE FROM PHENOL AND AMMONIA

[75] Inventor: Calvin J. Worrel, Detroit, Mich.

[73] Assignee: Ethyl Corporation, Richmond, Va.

[22] Filed: Oct. 2, 1969

[21] Appl. No.: 863,349

[52] U.S. Cl. ............................. 260/578; 260/247; 260/293.72; 260/326.15; 260/346.2 R; 260/570 R; 260/576; 260/577

[51] Int. Cl.$^2$ ................... C07C 87/52; C07C 87/56; C07C 87/62; C07C 87/64

[58] Field of Search ............... 260/578, 581, 585 B; 252/438

[56] References Cited
UNITED STATES PATENTS 2,000,410  5/1935  Morrell et al. ..................... 260/581
3,565,940  2/1971  Brown et al. .................... 252/438 X

*Primary Examiner*—Lewis Gotts
*Assistant Examiner*—S. P. Williams
*Attorney, Agent, or Firm*—Donald L. Johnson; Robert A. Linn; Joseph D. Odenweller

[57] ABSTRACT

Aromatic amines are made by reacting a phenol with aluminum nitride and either ammonia or a primary or secondary amine at temperatures from 200°–600°C. For example, 2,6-dimethyl-phenol reacts with aluminum nitride and ammonia to yield 2,6-dimethylaniline.

7 Claims, No Drawings

PREPARATION OF ANILINE FROM PHENOL AND AMMONIA

BACKGROUND

The conversion of hydroxy aromatic compounds, referred to collectively as phenols, to the corresponding aromatic amines has been accomplished in the past by such means as the Bucherer reaction, in which phenols are reacted with a bisulfite salt and ammonia. In British Pat. No. 619,877, certain phenols were converted to aromatic amines by reaction with ammonia and ammonium chloride. However, in some cases the desired aromatic amine is not readily available from prior methods. For example, 2,6-dimethylaniline cannot readily be made by reduction of the corresponding nitro derivative because the nitro derivative is not readily available. Also, even the reaction described in the above British patent gives but trace amounts of 2,6-dimethylaniline when applied to 2,6-dimethylphenol.

SUMMARY

It has not been discovered that aromatic amines can be prepared by reacting a phenol with aluminum nitride and ammonia or a primary or secondary amine at temperatures in the range of from about 200°–600°C.

DESCRIPTION OF THE PREFERRED EMBODIMENTS

A preferred embodiment of this invention is a process comprising reacting a phenol with aluminum nitride and a nitrogen compound selected from the group consisting of ammonia and amines having at least one hydrogen atom bonded to the amine nitrogen atom in a temperature range of from about 200°–600°C.

The phenol reactants may be in general any aromatic compound having a hydroxyl radical bonded to a benzene ring. The remainder of the molecule can be anything as long as it does not interfere with the process. For example, the aryl portion of the molecule may be a di- or tri- nuclear aromatic radical or, for that matter, it can contain even more aryl groups. The aryl portion of the phenol may be fused to other cyclic systems including heterocyclic systems such as cyclic systems containing oxygen, nitrogen and sulfur. For example, the phenols can be any of the isomeric hydroxy-substituted derivatives obtained by substituting a hydroxy group into an aromatic nucleus of benzene, naphthalene, anthracene, phenanthrene, indene, isoindene, benzofuran, isobenzofuran, thionaphthene, indole, isoindole, indolenine, 2-isobenzazole, 1,2-benzodiazole, 1,3-benzo-diazole, indiazine, 1,3-benzoisodiazole, 1,2,3-benzotriazole, benzisoxazole, benzoxadiazole, 1,2-benzopyran, 1,4-benzopyran, 1,2-benzopyrone, quinoline, isoquinoline, 1,3-benzodiazine, 1,2-benzisoxazine, acenaphthene, fluorene, dibenzopyrrole, xanthene, thianthrene, phenothiazine, phenoxazine, naphthacene, chrysene, pyrene, triphenylene, and the like, wherein the hydroxyl group is bonded to a nuclear carbon atom.

The following serve to further illustrate the phenol reactants obtained by inserting a hydroxyl group in a few of the above aromatic nuclei. These include phenol, α-naphthol, β-naphthol, 9-hydroxyanthracene, α-hydroxyanthracene, β-hydroxyanthracene, 2-hydroxyphenanthrene, 3-hydroxyphenanthrene, 7-hydroxyindene, 7-hydroxyisoindene, 7-hydroxybenzofuran, 4-hydroxybenzofuran, 5-hydroxyisobenzofuran, 6-hydroxythionaphthene, 7-hydroxyindole, 4-hydroxyisoindole, and the like. Phenols obtained by inserting a hydroxyl radical in the remaining aromatic nuclei will be apparent from the foregoing.

The process is also applicable to aryl hydroxy compounds having more than one hydroxyl radical bonded to a nuclear aromatic carbon atom, For example, the process can be applied to such polyhydroxy aromatics as hydroquinones, recorcinols, catechols, 1,3-dihydroxy naphthalenes, pyrogallols, phloroglucinols, and the like.

Substituents other than hydroxyl groups may be present in the aromatic compounds as long as they do not interfere with the course of the reaction. That is to say, the other substituents should be relatively inert to aluminum nitride, ammonia, primary or secondary amines. For example, any of the previously-listed aromatics may be substituted in a variety of positions with alkyl radicals aralkyl radicals, cycloalkyl radicals, chlorine, bromine, iodine, fluorine, nitro groups, and the like. A few representative examples of these using the simpler aromatic structures are p-chlorophenol, p-nitrophenol, β-bromo-α-naphthol, β-chloro-7-hydroxy-coumarone, 2-acetoxy-7-hydroxy-indolenine, 3-n-dodecyl-7-hydroxy-benzisoxazole, 4-nitro-8-hydroxy-1,2-benzopyran, 7-sec-octadecyl-8-hydroxy-isocoumarin, and the like.

The reaction proceeds very well when the hydroxy aromatic is a hydroxy-substituted mononuclear aromatic. As previously stated, these phenol type materials can be substituted with other groups as long as they do not interfere with the course of the reaction. A preferred class of such mononuclear hydroxy aromatics are those having the formula:

I wherein $n$ is an integer from 0–3, $m$ is an integer from 1–3, and $R_1$ is selected from the group consisting of alkyl radicals containing from 1–20 carbon atoms, aralkyl radicals containing from 7–20 carbon atoms, aryl radicals containing from 6–20 carbon atoms, and cycloalkyl radicals containing from 6–20 carbon atoms. Some examples of these are: phenol, catechol, recorcinol, pyrogallol, phluoroglucinol, hydroquinone, 3,5-di-tert-butylphenol, 2,6-di-tert-butylhydroquinone, 3-methyl catechol, p-cresol, m-cresol, p-eicosylphenol, 2,4-didodecylphenol, 2,4-dicyclohexylphenol, p-phenylphenol, p-(α-naphthyl)phenol, m-(2,4-di-sec-heptylphenyl)phenol, p-cyclohexylphenol, 3-cyclooctylphenol, p-(4-sec-dodecylcyclohexyl)phenol, 2,4,6-tri-methyl phluoroglucinol, m-sec-eicosylphenol, p-(4-tert-tridecylbenzyl)phenol, 4-(3,5-di-sec-heptylcyclohexyl)phenol, 4-phenylphenol, 4-(α-naphthyl) phenol, and 2-sec-eicosylhydroquinone.

The advantages of the process over the prior art methods display themselves to a greater extent when the hydroxy aromatic is a mononuclear phenol in which at least one position ortho to the phenolic hydroxyl radical is substituted with a radical selected from the group consisting of alkyl radicals containing from 1–20 carbon atoms, aryl radicals containing from 6–20 carbon atoms, cycloalkyl radicals containing from 6–20 carbon atoms and aralkyl radicals containing from 7–20 carbon atoms. These are phenols having the formula:

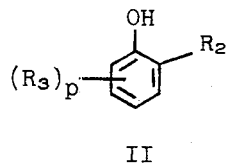

II wherein p is an integer from 0–2, $R_2$ and $R_3$ are selected from the group consisting of alkyl radicals containing from 1–20 carbon atoms, aralkyl radicals containing from 7–20 carbon atoms, aryl radicals containing from 6–20 carbon atoms and cycloalkyl radicals containing from 6–20 carbon atoms. Some further examples of these phenolic starting materials are:

o-sec-butylphenol,
2,5-dimethylphenol,
o-cresol,
o-ethylphenol,
2,4,6-tri-sec-butylphenol,
2,4-dimethylphenol,
2-(α-methylbenzyl)phenol,
2-cyclohexyl-p-cresol,
2-cyclooctylphenol,
2(3,5-di-tert-butyl-cyclohexyl)-4-sec-eicosylphenol,
2-sec-eicosylphenol,
2-(α-methyl-4-dodecylbenzyl)phenol,
2-phenylphenol,
2-naphthylphenol,
2(4-tetradecylphenyl)phenol,
2(3,5-di-sec-heptylphenyl)phenol,
2-tert-octadecylphenol,
2-isopropylphenol,
2-β-naphthylphenol,
2,4-di-sec-dodecylphenol,
2-(p-sec-tetradecylcyclohexyl)-4-methylphenol, and
2-(α-methyl-4-sec-amylbenzyl)phenol.

An especially valuable feature of this invention is its ability to replace an aromatic hydroxyl radical with an amine radical when both positions on the aromatic nucleus ortho to the hydroxyl group are substituted. When the aromatic hydroxy compound is a mononuclear phenol the phenolic reactant used in this embodiment of the invention has the formula:

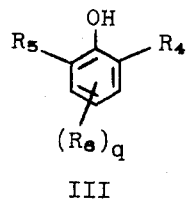

III wherein q is 0 or 1, and $R_4$, $R_5$ and $R_6$ are selected from the same group as $R_2$ in Formula II. Some examples of these phenols are:

2,6-dimethylphenol,
2,4,6-trimethylphenol,
2,6-di-sec-butylphenol,
2,6-di-sec-butyl-p-cresol,
2,4-dimethyl-6-sec-butylphenol,
2,6-diisopropylphenol,
2,6-di-sec-octylphenol,
2,6-di(α-methylbenzyl)phenol,
6(α-methylbenzyl)-o-cresol,
2,4-di-methyl-6-(2,3-benzobenzyl)phenol,
2(3-tert-butyl-5-isopropylbenzyl)phenol,
2,6-dicyclooctylphenol,
2,6-dibornylphenol,
2,6-dicyclohexylphenol,
2,6-dieicosylphenol,
6-sec-eicosyl-o-cresol,
2,4-dimethyl-6-docosylphenol,
6-phenyl-o-cresol,
2,4-dimethyl-6-(4-tetradecylphenyl)phenol,
2-ethyl-6-(3,5-diheptylphenyl)-p-cresol, and the like.

Another reactant in the process is either ammonia or an amine having at least one hydrogen atom bonded to the amine nitrogen atom. These are generally referred to as primary or secondary amines. Examples of these amines are dimethyl amine, methyl amine, ethyl amine, diethyl amine, n-propyl amine, aniline, α-naphthyl amine, piperidine, morpholine, diethanol amine, ethanol amine, n-dodecyl amine, 2-docosyl amine, n-triacontyl amine, 1-pentacontyl amine, and the like. Polyamines and polyalkylene amines are also useful. Examples of these amines are N,N-dimethyl-1,3-propanediamine, ethylene diamine, 1,6-hexane diamine, diethylene triamine, triethylene tetraamine, tetraethylene pentamine, and the like. When amines having multiple NH or $NH_2$ groups available are used the process can be carried out in a manner to utilize more than one of the available amine groups. For example, the reaction of phenol, aluminum nitride and ethylene diamine can be carried out to form N,N'-diphenyl ethylene diamine. Likewise, 1,6-hexane diamine will form N,N'-diphenyl-1,6-hexane diamine. Likewise, tetraethylene pentamine will form a mixture in which the terminal nitrogen atoms are substituted with a phenyl radical.

A preferred class of nitrogen compounds are those having the formula:

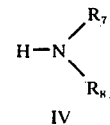

IV in which $R_7$ and $R_8$ are selected from hydrogen, alkyl radicals containing 1–20 carbon atoms, cycloalkyl radicals containing 6–20 carbon atoms or aryl radicals containing 6–20 carbon atoms, and radicals having the formula:

V wherein $R_9$ is an alkylene radical containing 2–4 carbon atoms and r is an integer from 1–5. A few further examples of the foregoing are methyl ethyl amine, n-eicosyl amine, ammonia, cyclohexyl amine, cyclooctyl amine, 4-sec-tetradecylcyclohexyl amine, aniline, N-methyl aniline, ethylene diamine, 1,2-propylene diamine, diethylene triamine, pentaethylene hexamine, 1,4-butane diamine, and the like.

The most preferred nitrogen compound is ammonia.

Various metal nitrides can be used such as magnesium nitride, boron nitride, manganese nitride, calcium nitride, nickel nitride, cobalt nitride, barium nitride, titanium nitride, zirconium nitride, niobium nitride, tantalum nitride, vanadium nitride, copper nitride, molybdenum nitride, tungsten nitride, chromium nitride, and the like. Of these, the most preferred is aluminum nitride. Aluminum nitride is a known compound which can be formed by the reaction of aluminum metal and nitrogen or nitrogen compounds such as ammonia at temperatures over 800°C.

The process of this invention can be carried out by merely mixing the reactants and heating them to reaction temperature. Alternatively, a mixture of the phenol and nitrogen compound can be passed through a bed of aluminum nitride heated to reaction temperature.

The ratio of reactants is not critical. Generally, it is preferred to have from 0.5–10 moles of the nitrogen compound and 0.3–10 moles of aluminum nitride per mole of phenol, although more or less of each reactant can be used.

The reaction proceeds at elevated temperatures. In general, temperatures over 200°C. and below the decomposition temperature of the reactants and products are satisfactory. A preferred temperature range is from about 200°–600°C., and a most preferred range is from about 300°–550°C.

When carried out by mixing the reactants and heating to reaction temperatures the reaction is generally under pressure. The pressure results from the vapor pressure of the reactants at the reaction temperature. The pressure range can be from about 0–10,000 psig, depending upon the reactants and temperature. When carried out by passing the phenol and nitrogen reactants through a heated bed of aluminum nitride the pressure can also be maintained above atmospheric, although under these conditions this is not necessary as the phenol and nitrogen reactant can merely pass through the aluminum nitride bed as vapors. If pressures are employed in this method a useful range is from atmospheric up to about 10,000 psig.

The reactants should be maintained in contact until the desired conversion to product is attained. This depends to some extent upon reaction temperatures. In general, satisfactory conversions are obtained in from about 2 to 16 hours.

The following examples serve to illustrate the manner in which the process is conducted. All parts are by weight unless otherwise specified.

EXAMPLE 1

In a pressure reaction vessel previously purged with nitrogen was placed 244 parts of 2,6-dimethylphenol, 54 parts of aluminum nitride and 80 parts of ammonia. The vessel was sealed and, while stirring, heated to 350°C. The pressure reached 4300 psig. After 8 hours, the vessel was cooled and the contents diluted with 300 parts of hexane. The diluted reaction mixture was discharged from the reaction vessel and extracted with dilute hydrochloric acid. The free 2,6-dimethylaniline product was recovered from the acid extract by neutralization, giving a 17 per cent conversion and 77.4 per cent yield of 2,6-dimethylaniline.

EXAMPLE 2

A series of four runs was carried out in the same manner as employed in Example 1. The maximum pressure reached in each case ranged from 2850°–4300 psig. The average conversion of 2,6-dimethylphenol to 2,6-dimethylaniline obtained in the four runs was 30 per cent and the average yield based on consumed 2,6-dimethylphenol was 82 per cent.

Other phenols can be substituted in the above examples with good results. For example, $\alpha$-naphthol forms $\alpha$-naphthylamine; $\beta$-naphthol forms $\beta$-naphthylamine; p-cresol forms p-methyl-aniline; p-tert-butylphenol forms p-tert-butylaniline; o-isopropylphenol forms o-isopropylaniline; o-tert-butylphenol forms o-tert-butylaniline; 2,6-di-tert-butylphenol forms 2,6-di-tert-butylaniline; 2,6-diethylphenol forms 2,6-diethylaniline; o-cyclohexylphenol forms o-cyclohexylaniline; o-phenylphenol forms o-phenylaniline; o-($\alpha$-methylbenzyl)phenol forms o-($\alpha$-methylbenzyl)aniline; $\alpha$-hydroxyanthracene forms $\alpha$-aminoanthracene. From this, it can be seen that a wide variety of phenolic reactants such as those previously described can be readily converted to the corresponding amine derivative in a manner illustrated in the above examples.

EXAMPLE 3

A tubular reactor, 6 feet long and one inch in diameter, is filled with a granular aluminum nitride. This reactor is heated to 550°C. and an equal mole mixture of o-cresol and ammonia is pumped into one end of the reactor. The rate of addition of the mixture is 100 grams per hour. The vapors emerging from the other end of the reactor are condensed and the resultant mixture dissolved in hexane. After 12 hours of operation the hexane is extracted with dilute hydrochloric acid and the product, o-methylaniline, recovered by neutralization of the acid extract.

Good results can be obtained following the above procedure using other nitrogen compounds such as methylamine forming o-methyl-N-methylaniline; dimethylamine forming o-methyl-N,N-dimethylaniline; ethylamine forming o-methyl-N-ethylaniline, and the like.

EXAMPLE 4

This example is conducted in a manner similar to that of Example 3 except that the rate of the reaction mixture leaving the reactor is controlled by a pressure regulating valve such that the reactor pressure is maintained at 5000 psig. Product is recovered in the same manner, yielding o-methylaniline in high conversion and yield.

The amines made by this process are useful for a variety of purposes. They are intermediates for antioxidants, antiozonants, dyes, herbicides and insecticides.

The lower molecular weight gasoline-soluble aniline derivatives are useful antiknock agents for spark ignited internal combustion engines (Ind. Eng. Chem., 47, page 2141, 1955). For example, N-methylaniline made from phenol, aluminum nitride and methylamine by the process of this invention is an excellent antiknock agent. Likewise, 2,4-dimethylaniline made from 2,4-di-methylphenol, aluminum nitride and ammonia is also a very effective antiknock agent. In this use, they are added to a liquid hydrocarbon fuel of the gasoline boiling range in an antiknock amount, generally from 0.25 to 1 per cent.

In U.S. Pat. No. 3,322,810 is described certain 2,6-dialkyl isothiocyanates which are useful as pesticides. The isothio-cyanates are made by reacting carbon disulfide with a 2,6-dialkyl-aniline. These anilines are readily made by the present process. For example, 2,6-dimethylaniline is made in good yield from the corresponding 2,6-dimethylphenol, as shown in Example 1.

The compounds made by this invention are also intermediates in the manufacture of polyurethanes. These polymers are made by reacting aromatic diisocyanates with polyhydroxy compounds. The diisocyanates are in turn made by the reaction of diamino aromatics with phosgene. The present invention provides a good process for the preparation of the diamino aromatic from the corresponding dihydroxy aromatic. For example, 4,4'-diisocyanato-3,3',5,5'-tetramethyl diphenylmethane is readily made by either (1) reacting 4,4'-dihydroxy-3,3',5,5'-tetramethyl diphenylmethane with aluminum nitride and ammonia at 200°–600°C., or (2) reacting 2,6-dimethylphenol with aluminum nitride and ammonia to form 2,6-dimethylaniline and subsequently coupling this aniline at the 4 position through a methylene bridge by reaction with formaldehyde.

I claim:

1. A process for making aromatic amines, said process comprising reacting a phenol with aluminum nitride and ammonia in a temperature range of from about 200°–600°C.

2. A process of claim 1 wherein said phenol is a mononuclear phenol.

3. A process of claim 2 wherein said temperature range is from about 300°–550°C.

4. A process of claim 3 wherein said mononuclear phenol is substituted in at least one nuclear position ortho to the phenolic hydroxyl radical with a group selected from alkyl radicals containing 1–20 carbon atoms, cycloalkyl radicals containing 6–20 carbon atoms, aryl radicals containing 6–20 carbon atoms or aralkyl radicals containing 7–20 carbon atoms.

5. A process of claim 4 wherein said mononuclear phenol is a 2,6-dialkylphenol in which the alkyl groups contain 1 to about 20 carbon atoms.

6. A process of claim 5 wherein said 2,6-dialkylphenol is 2,6-dimethylphenol.

7. A process of claim 6 wherein said temperature range is from about 300°–550°C.

* * * * *